United States Patent
Yagi et al.

(10) Patent No.: US 6,837,244 B2
(45) Date of Patent: Jan. 4, 2005

(54) OXYGEN ENRICHING APPARATUS, CONTROLLER FOR THE OXYGEN ENRICHING APPARATUS, AND RECORDING MEDIUM FOR THE CONTROLLER

(75) Inventors: Hideaki Yagi, Aichi (JP); Takahito Kojima, Aichi (JP); Junichi Akiyama, Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 126 days.

(21) Appl. No.: 09/956,924

(22) Filed: Sep. 21, 2001

(65) Prior Publication Data

US 2002/0038656 A1 Apr. 4, 2002

(30) Foreign Application Priority Data

Sep. 21, 2000 (JP) .................................... 2000-287108

(51) Int. Cl.[7] .............................. A62B 7/00; A62B 9/00; G05B 1/00
(52) U.S. Cl. .............................. 128/205.11; 128/204.23; 128/204.26
(58) Field of Search ..................... 128/205.11, 204.26, 128/204.21, 204.23, 204.18, 204.76

(56) References Cited

U.S. PATENT DOCUMENTS

| | | | | |
|---|---|---|---|---|
| 4,681,099 A | * | 7/1987 | Sato et al. | 128/204.23 |
| 4,686,974 A | * | 8/1987 | Sato et al. | 128/204.23 |
| 4,706,664 A | * | 11/1987 | Snook et al. | 128/204.23 |
| 5,137,017 A | * | 8/1992 | Salter | 128/207.18 |
| 5,626,131 A | * | 5/1997 | Chua et al. | 128/204.23 |
| 5,720,276 A | | 2/1998 | Kobatake et al. | 128/204.18 |
| 6,237,594 B1 | * | 5/2001 | Davenport | 128/204.26 |
| 6,378,520 B1 | * | 4/2002 | Davenport | 128/204.26 |

FOREIGN PATENT DOCUMENTS

JP 8-187289 7/1996 .......... A61M/16/00

* cited by examiner

Primary Examiner—Henry Bennett
Assistant Examiner—Andrea M. Ragonese
(74) Attorney, Agent, or Firm—Sughrue Mion, PLLC

(57) ABSTRACT

A small oxygen enriching apparatus which can supply oxygen-enriched gas at high flow rate without imparting unnatural sensation to a user, as well as a controller and recording medium therefore. In step 100, a judgment is made as to whether a flow rate set by use of a flow-rate setting unit 47 is equal to or less than a continuous base flow rate (2 liters/min). When the set flow rate is a low flow rate of not greater than 2 liters/min, breath-synchronized operation is not performed (continuous supply is to be performed), and therefore, in step 110, oxygen-enriched gas is supplied continuously at the set flow rate. When the set flow rate is a high flow rate of greater than 2 liters/min, breath-synchronized operation is to be performed (supply during the inhalation period only of each breathing cycle), and therefore, in step 120, oxygen-enriched gas is continuously supplied at the continuous base flow rate. In step 140, in order to perform breath-synchronized operation, control for opening and closing an electromagnetic valve 45 is performed. That is, oxygen-enriched gas is supplied during the inhalation period only of each breathing cycle, and supply of oxygen-enriched gas is stopped during the exhalation period.

11 Claims, 6 Drawing Sheets

[FIG. 1]
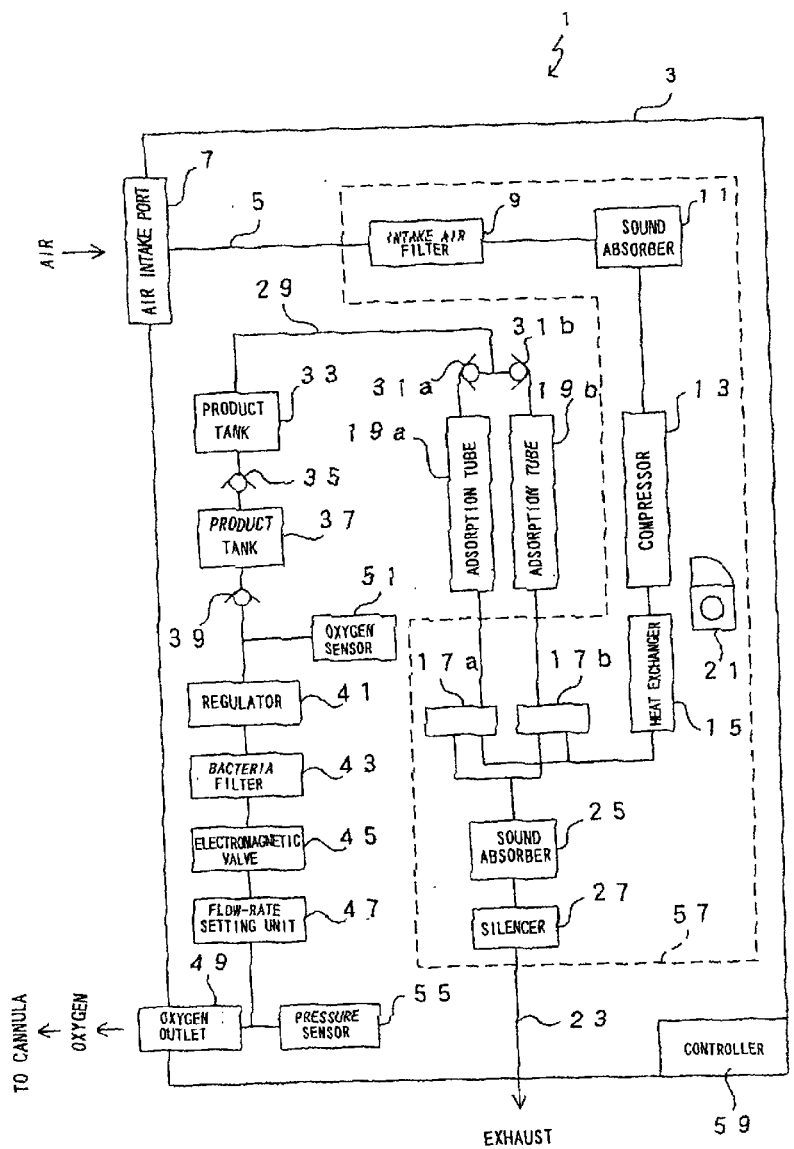

[FIG. 2]
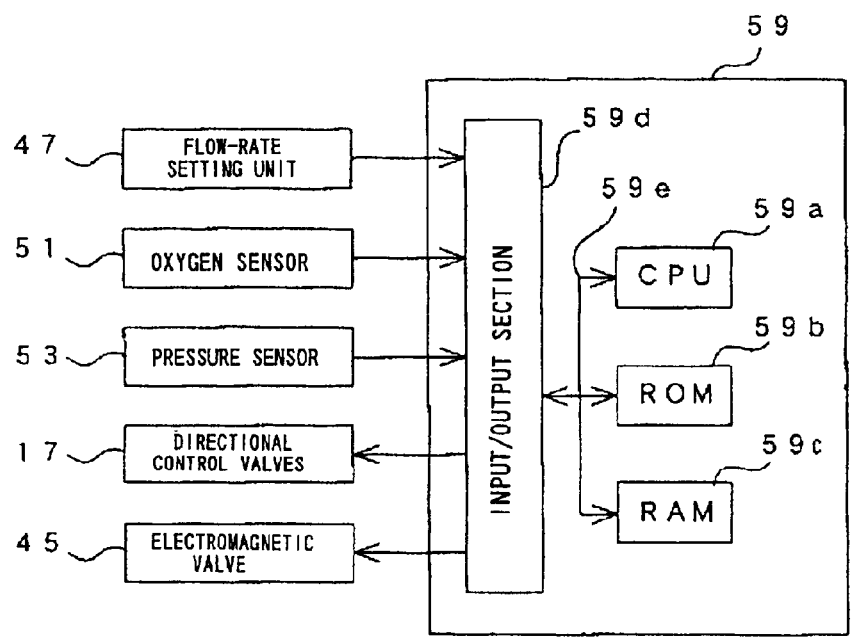

[FIG. 3]
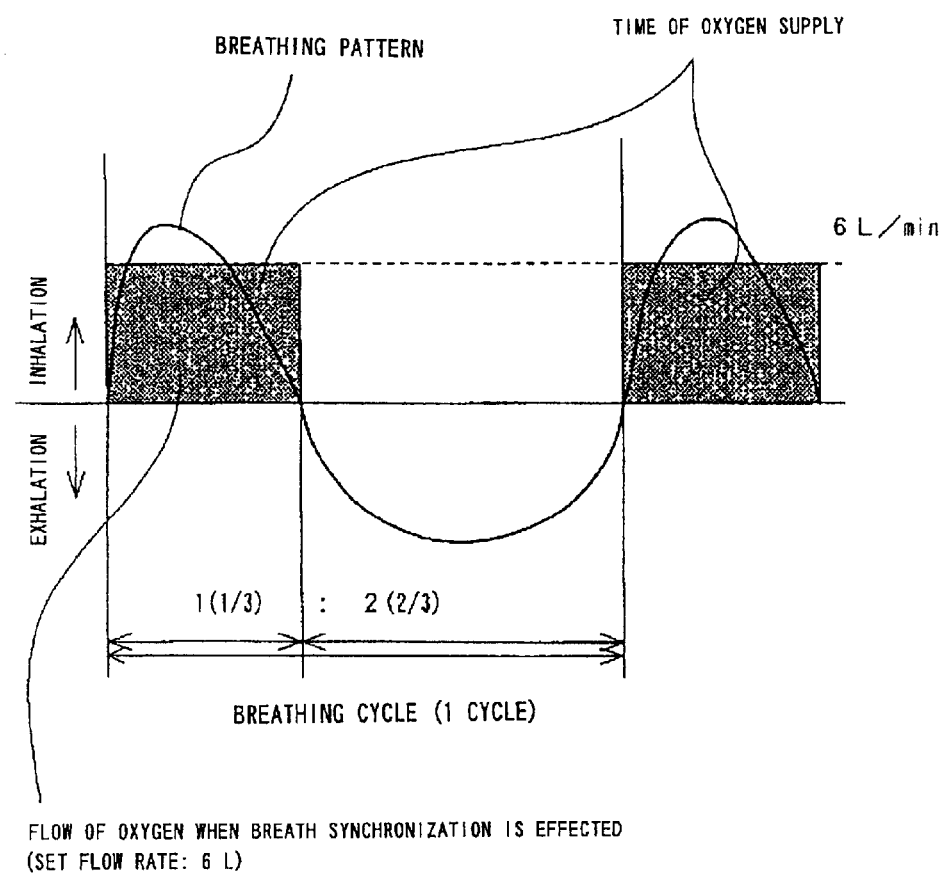

[FIG. 4]
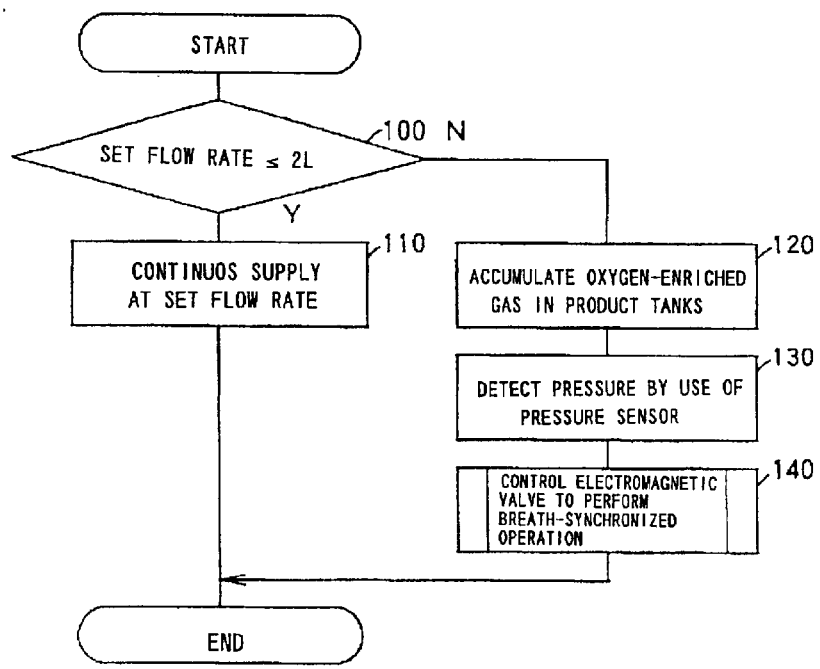

[FIG. 5]
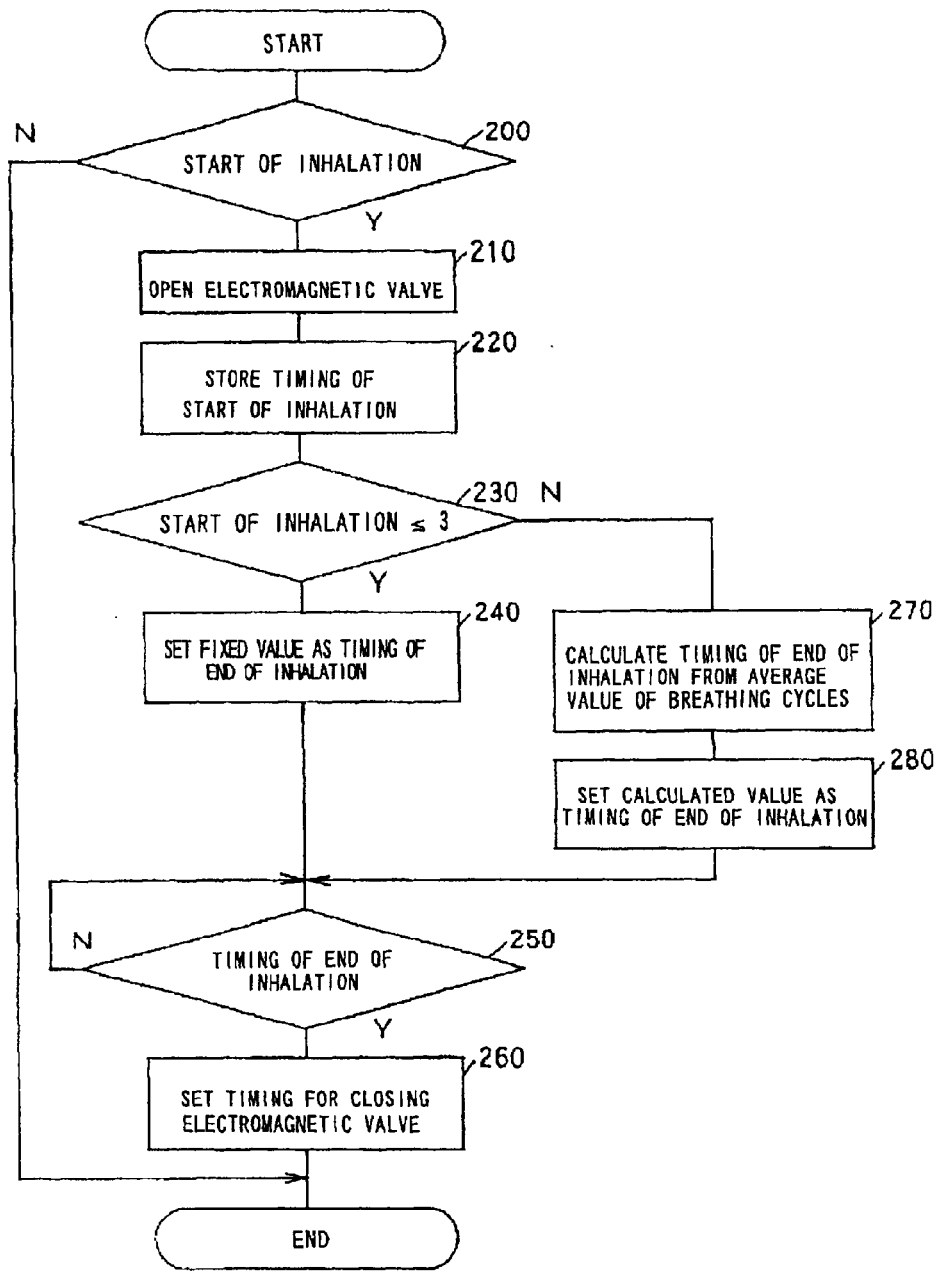

[FIG. 6]
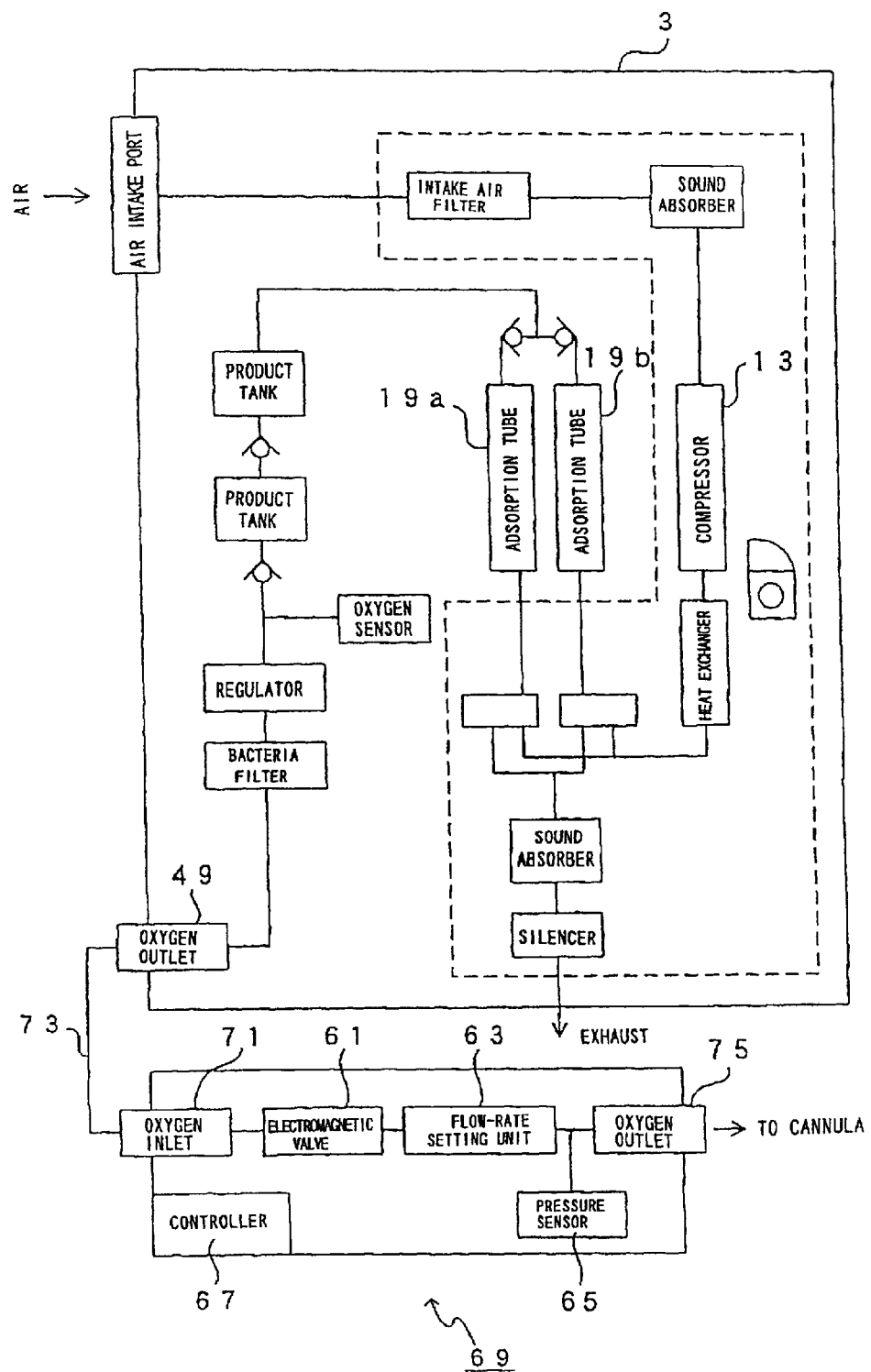

OXYGEN ENRICHING APPARATUS, CONTROLLER FOR THE OXYGEN ENRICHING APPARATUS, AND RECORDING MEDIUM FOR THE CONTROLLER

FIELD OF THE INVENTION

The present invention relates to an oxygen enriching apparatus (or oxygen concentrator) capable of producing high-concentration oxygen from, for example, air through adsorption removal of nitrogen from the air and supplying the high-concentration oxygen to, for example, a patient. The present invention further relates to a controller for the oxygen enriching apparatus and a recording medium for the controller.

DESCRIPTION OF THE RELATED ART

Conventionally, an oxygen enriching apparatus for medical use capable of producing an oxygen-enriched gas from, for example, air through adsorption removal of nitrogen from the air and supplying high-concentration oxygen to a patient has been used in, for example, home care oxygen therapy.

Since a patient who uses such an oxygen enriching apparatus is weak in lung function as compared with healthy persons, the patient must use the oxygen enriching apparatus all day long. Therefore, an oxygen enriching apparatus which can be used conveniently for daily living has been in demand.

When the condition of the patient is good, the flow rate of the oxygen-enriched gas (hereinafter may be referred to as "oxygen flow rate") is typically set to 2 liters/min or less (hereinafter "min" may be omitted), and this flow rate is sufficient. However, when the condition of the patient becomes worse, an oxygen flow rate of greater than 2 liters/min is required, and in order to provide a margin for safety, an oxygen flow rate of about 5 to 7 liters/min is required.

PROBLEMS SOLVED BY THE INVENTION

When the capacity of the oxygen enriching apparatus is increased, the oxygen-enriched gas can be supplied at a higher flow rate. However, in such a case, the size of the oxygen enriching apparatus increases, raising the following problems (1) to (3).

(1) Since the volume and weight of the oxygen enriching apparatus increase, a large burden is imposed on a caregiver when he or she transports or moves the oxygen enriching apparatus.

In an example case in which a caregiver or a sales representative transports the oxygen enriching apparatus to the patient's house and installs it there, the caregiver or sales representative cannot perform the installation work by himself because of the large size of the apparatus, and the caregiver or sales representative must bear a considerably large burden.

(2) Due to increased consumption of electrical power, the charge for electricity increases, with a resultant increase in cost.

For example, the electrical-power consumption of an oxygen enriching apparatus having a capacity of 5 to 7 liters (5 to 7 liter model) (450W) is about two times that of a conventional 2 liter or 3 liter model.

(3) Increased noise hinders good sleep of the patient. When a measure for the noise is employed, the volume and weight of the oxygen enriching apparatus increase further.

For example, if a soundproofing material is disposed as a measure against noise during operation, the volume and weight of the oxygen enriching apparatus increase further, and the increased weight (45 Kg) is about two times that of the conventional 2 liter or 3 liter model. However, in spite of providing the soundproofing material, the noise level is still high, thus failing to guarantee that the patient will sleep well.

That is, conventional oxygen enriching apparatus for medical use and ordinary oxygen enriching apparatus are based on the same design concept. Therefore, when oxygen is to be supplied at a flow rate of 5 liters/min, the capacity of a compressor and the amount of an adsorbing material for adsorbing nitrogen must be increased. Also, an electromagnetic valve of a larger diameter suitable for the increased flow rate must be used as an electromagnetic valve for controlling feeding of compressed air from the compressor to the adsorbing material. Consequently, the sizes of components naturally increase, and the above-described problems (1) to (3) arise.

Apart from the above-described technique regarding oxygen enriching apparatus, a technique has been developed in which a patient carries an oxygen cylinder with him or her during travel or at the time of visiting a hospital.

In this technique, a breath synchronizer for supplying oxygen synchronous with breathing is used so as to reduce consumption of oxygen supplied from the cylinder, to thereby extend the service life of the oxygen cylinder.

The breath synchronizer utilizes the rule of thumb that in the case of a human the ratio between the inhalation period and the exhalation period is 1:2. Upon detection of inhalation by means of a sensor, the breath synchronizer supplies high-concentration oxygen from the oxygen cylinder over a short period of time (in the manner of a pulse).

This technique can reduce the consumption of oxygen stored in the oxygen cylinder and the consumption of drive batteries, because high-pressure oxygen is supplied from the oxygen cylinder only for a short period of time upon start of inhalation. However, the technique involves another problem in that the patient feels that something is wrong, because the breath synchronizer creates a breathing condition that differs from ordinary breathing conditions.

In recent years, a technique for applying the breath synchronization technique used with an oxygen cylinder to an oxygen enriching apparatus has been proposed (see, for example, Japanese Patent Application Laid-Open (kokai) No. 8-187289). However, effective ways for solving the above-described problems caused by the increased apparatus size have not been developed.

SUMMARY OF THE INVENTION

The present invention has been achieved to solve the above-described problems of the prior art. It is therefore an object of the present invention to provide a small oxygen enriching apparatus which can supply oxygen-enriched gas at high flow rate without imparting unnatural sensation to a user, as well as a controller and recording medium therefore.

The present inventors found that when a sensor for detecting, for example, inhalation is disposed in an oxygen enriching apparatus and breath-synchronized control is performed, theoretically, oxygen-enriched gas can be supplied at a flow rate of up to three times the continuous supply capacity of the oxygen enriching apparatus. The present inventors have completed the present invention based on this finding.

In an example case in which a breath synchronization function is added to an oxygen enriching apparatus having a supply capacity of 2 liters/min, theoretically, the oxygen enriching apparatus can increase the flow rate up to 6 liters/min. Therefore, the oxygen enriching apparatus can maintain the compactness, low electrical power consumption, and low noise of the 2 liter model, to thereby provide many advantages to a patient and caregivers.

The above objects have been achieved in a first embodiment of the invention, by providing:

(1) A oxygen enriching apparatus (or oxygen concentrator) which enriches (or concentrates) oxygen contained in air to thereby obtain oxygen-enriched gas, and which supplies the oxygen-enriched gas to a user synchronously with inhalation of the user by means of a breath synchronizing function, which comprises: means for supplying oxygen-enriched gas at a first flow rate equal to or less than a continuous base flow rate when a breath-synchronized operation is not performed, which represents a flow rate at which the oxygen enriching apparatus can supply the oxygen-enriched gas continuously; and means for supplying the oxygen-enriched gas at a second flow rate greater than the continuous base flow rate during an inhalation period having a length 25 to 40% that of a breathing cycle of the user when a breath-synchronized operation is performed.

In the present invention, the continuous base flow rate represents a continuously-supplyable flow rate (that is, a continuous supply capacity which represents the maximum flow rate at which the oxygen enriching apparatus can supply oxygen-enriched gas continuously). For example, in the case of a 2 liter model, the continuous base flow rate is set to 2 liters/min. When the breath-synchronized operation is not performed, the oxygen enriching apparatus continuously supplies oxygen-enriched gas to the user at a first flow rate equal to or less than the continuous base flow rate.

When the breath-synchronized operation is performed, the oxygen enriching apparatus supplies oxygen-enriched gas at a high flow rate (e.g., about 5 or 6 liters/min) greater than the continuous base flow rate over an inhalation period having a length 25 to 40% that of a breathing cycle (preferably ⅓ of the breathing cycle) of the user (e.g., a patient). Accordingly, the oxygen enriching apparatus supplies the oxygen-enriched gas intermittently in breathing cycles.

That is, when the breath-synchronized operation is performed, oxygen-enriched gas need not be supplied to the user during the exhalation period. Therefore, during that period, oxygen-enriched gas produced through, for example, adsorption of nitrogen can be accumulated in a tank or the like. Therefore, during the inhalation period, not only continuously-supplied oxygen-enriched gas but also a sufficient amount of oxygen-enriched gas accumulated during the exhalation period can be supplied to the user. Thus, the oxygen-enriched gas can be supplied to the user at a flow rate greater than the continuous base flow rate.

In addition, in the present invention, when the breath-synchronized operation is not performed (i.e., in the case of continuous supply), the oxygen enriching apparatus is merely required to supply oxygen-enriched gas at a low flow rate less than the continuous base flow rate. Therefore, the oxygen enriching apparatus can have a small body (lightweight and small volume) of, for example, a 2 or 3 liter model. In other words, in spite of the small body, the oxygen enriching apparatus can supply oxygen at a high flow rate when necessary (when the breath-synchronized operation is performed).

Therefore, the present invention achieves the following effects, among others. (1) Since the volume and weight of the oxygen enriching apparatus do not increase, the burden imposed on a sales representative or a caregiver can be decreased. (2) Since electrical-power consumption does not increase, electric power cost is low. (3) Since the level of noise is low, the noise does not hinder good sleep of the patient. In addition, even when a measure against the noise is employed, the volume and weight of the oxygen enriching apparatus do not increase very much.

Although the length of the inhalation period is generally about ⅓ the length of the breathing cycle, the length varies slightly depending on the user and his condition. In view of this, in the present invention, oxygen-enriched gas is supplied at a high flow rate during the inhalation period, which has a length 25 to 40% that of the user's breathing cycle.

That is, in the present invention, a sufficient amount of oxygen-enriched gas can be supplied to each user at a high flow rate over the inhalation period whose length varies depending on the user. Therefore, the user can breath without feeling any unnatural sensation.

The above-described "breath-synchronized operation" refers to an operation for supplying oxygen-enriched gas intermittently in order to substantially match the user's spontaneous inhaling action within each breathing cycle.

Example configurations for enriching oxygen include a configuration which uses, for example, an adsorbent for selectively adsorbing and removing nitrogen contained in air, and a configuration which uses a membrane that is permeable to oxygen.

Each of the above-described continuous base flow rate, first flow rate, and second flow rate is a unit flow rate which represents an amount of oxygen-enriched gas supplied over a certain time and can be represented by a volume of a gas (at 1 atm) supplied over, for example, 1 min.

The above-described inhalation period can be obtained on the basis of data detected by use of a sensor.

Notably, the present invention can be suitably applied to the case in which oxygen is supplied to a user by use of a so-called open system which uses a nasal cannula, for example.

(2) The invention in a second embodiment is characterized in that the continuous base flow rate is 4 liters/min or less.

That is, as described above, a small apparatus whose continuous base flow rate is 4 liters/min or less is excellent in terms of easiness of transport, electricity cost, and noise. In the present invention, even when a small apparatus whose continuous base flow rate is 4 liter/min or less is used, oxygen-enriched gas can be supplied at a flow rate (e.g., 5 to 7 liters/min) greater than the continuous base flow rate by performing the breath-synchronized operation. Therefore, the above-described advantages of a small apparatus can be obtained to the maximum extent.

(3) The invention in a third embodiment is characterized in that the oxygen enriching apparatus detects the state of inhalation or exhalation by use of the above-described sensor, and controls supply of the oxygen-enriched gas on the basis of a signal output from the sensor.

Pressure decreases (e.g., to a negative pressure of several $mmH_2O$) during inhalation, and increases (to a positive pressure) during exhalation. Accordingly, through detection of this pressure variation by use of a sensor, start and end of inhalation or start and end of exhalation can be detected.

Therefore, supply of oxygen-enriched gas by the above-described inhalation synchronization can be performed properly, on the basis of the state of inhalation or exhalation detected by use of the sensor.

An example of the sensor is a pressure sensor for detecting pressure variation caused by inhalation or exhalation. Examples of such a pressure sensor include a diaphragm-type pressure sensor and a sensor which detects pressure or differential pressure from variation in electrostatic capacitance.

(4) The invention in a fourth embodiment is characterized in that the oxygen enriching apparatus determines a timing for staring or ending supply of the oxygen-enriched gas in the breathing cycle, based on the signal from the sensor.

The present embodiment exemplifies a timing to be detected by the sensor.

(5) The invention in a fifth embodiment is characterized in that the oxygen enriching apparatus detects the state of inhalation or exhalation one time or a plurality of number of times based on the signal output from the sensor, and determines the timing for starting or ending subsequent supply of the oxygen-enriched gas on the basis of the thus-detected state of inhalation or exhalation.

In the present embodiment, the timing for starting or ending the supply of the oxygen-enriched gas is determined on the basis of stored past data.

For example, since the length of a single breathing cycle can be found by measuring the time between the start of a first inhalation and the start of a second inhalation, in the next breathing cycle, a predetermined period (e.g., a period of ⅓ the breathing cycle) starting from the start of inhalation is set as an inhalation period, and oxygen-enriched gas is supplied at a high flow rate over the inhalation period. Preferably, this operation is repeated continuously.

Since the above operation enables accurate supply of oxygen-enriched gas over the user's inhalation period, the user does not feel any unnatural sensation.

Notably, a predetermined, fixed value may be used as the length of the inhalation period until the length of the inhalation period is calculated from the data.

Moreover, since accuracy in calculating the length of the inhalation period can be increased by use of an average of a plurality of data sets, the length of the inhalation period may be updated continuously by use of, for example, an average of a plurality of past data sets.

(6) The invention in a sixth embodiment is characterized in that a tank is provided in the oxygen-enriched-gas supply passage on the downstream side of an oxygen enriching section (e.g., a section in which nitrogen is adsorbed for enrichment), in order to accumulate oxygen-enriched gas supplied during the exhalation period of the breathing timing.

Accordingly, in the present embodiment, a sufficient amount of oxygen-enriched gas can be accumulated in the tank during each exhalation period.

That is, since the ratio between the inhalation period and the exhalation period is generally 1:2, in the case of a 2 liter model whose continuous base flow rate is 2 liters/min, oxygen-enriched gas can be accumulated in the tank during the exhalation period so as to enable supply of the oxygen-enriched gas at 4 liters/min (during subsequent breath-synchronized operation).

Therefore, theoretically, oxygen-enriched gas can be supplied at 6 liters/min, which is the sum of the continuous base flow rate (2 liters/min) and the supply capacity of the tank (4 liters/min); i.e., three times the continuous base flow rate.

(7) The invention in a seventh embodiment is characterized in that a plurality of tanks are provided in series in the oxygen-enriched-gas supply passage, on the downstream side of the oxygen enriching section, for stable supply of oxygen-enriched gas.

When a small apparatus (e.g., having a continuous base flow rate of 2 or 3 liters/min) supplies oxygen-enriched gas intermittently at a high flow rate by performing the breath-synchronized operation, pressure fluctuations stemming from start and stop of supply of the oxygen-enriched gas may influence the oxygen enriching section. In the present embodiment, since a plurality of serially connected tanks are provided, if such pressure fluctuations are generated, the tanks absorb the pressure fluctuations.

Accordingly, since pressure fluctuations do not influence the oxygen enriching section, stable oxygen enriching (e.g., adsorption of nitrogen) can be performed, and thus oxygen-enriched gas can be supplied stably.

(8) The invention in an eighth embodiment is characterized in that each of two tanks connected in series has a capacity of at least 500 ml (e.g., about 750 ml).

The present embodiment exemplifies the volume of tanks provided in a small apparatus (e.g., 2 liter model) whose continuous base flow rate of oxygen-enriched gas is 2 liters/min. When the tanks have the above-described capacity, the tanks can accumulate a sufficient amount of oxygen-enriched gas during each exhalation period.

That is, in the case of a 2 liter model, when two serially connected tanks each having a capacity of 500 ml or more are provided, the above-described influence of pressure fluctuations can be effectively prevented.

(9) The invention in a ninth embodiment is characterized in that a check valve for preventing reverse flow toward the oxygen enriching section is disposed between the plurality of tanks.

Accordingly, even when the above-described pressure fluctuations are generated, their propagation can be prevented by the check valve, so that adverse effect of the pressure fluctuations can be prevented.

(10) The invention in a tenth embodiment is characterized in that a switch (manual switch) for setting a flow rate of oxygen-enriched gas is provided. When the flow rate is set by use of the switch to the first flow rate equal to or less than the continuous base flow rate, the oxygen enriching apparatus supplies the oxygen-enriched gas continuously. When the flow rate is set by use of the switch to the second flow rate greater than the continuous base flow rate, the oxygen enriching apparatus supplies the oxygen-enriched gas by means of the breath-synchronized operation.

In an example case in which the continuous base flow rate is 2 liters/min, the first flow rate (which is a flow rate for continuous supply) can be set to a desired value through operation of the manual switch if the desired value is not greater than 2 liters/min.

Further, when the flow rate is set by use of the manual switch to a value greater than 2 liters/min, the control mode is automatically switched to the mode for performing breath-synchronized operation. In an example case in which the flow rate is set to 5 liters/min, the breath-synchronized operation is performed such that oxygen-enriched gas is supplied at 5 liters/min during each inhalation period.

(11) The invention in an eleventh embodiment is directed to a controller for controlling operation of the oxygen enriching apparatus. The controller may be integrated with (built in) the oxygen enriching apparatus or may be separated from the oxygen enriching apparatus.

(12) The invention in a twelfth embodiment is directed to a recording medium having recorded thereon means (e.g., a program) for executing the function of the controller.

When the function of the controller is executed by use of a computer system, the function can be provided in the form of a program which is executed in the computer system. Such a program can be recorded on a computer-readable medium, such as a floppy disk, a magnetic optical disk, CD-ROM, or a hard disk drive, and when necessary can be loaded on the computer system and started so as to use the program. Alternatively, the program may be stored in ROM or backup RAM serving as a computer-readable recording medium, which is then incorporated into the computer system.

BRIEF DESCRIPTION OF THE DRAWINGS

FIG. 1 is an explanatory view showing the basic structure of an oxygen enriching apparatus of an embodiment of the invention.

FIG. 2 is a block diagram showing the electrical configuration of a controller of the oxygen enriching apparatus of the embodiment.

FIG. 3 is an explanatory view showing breathing cycles.

FIG. 4 is a flowchart showing the basic control processing performed by the controller of the embodiment.

FIG. 5 is a flowchart showing the electromagnetic-valve control processing performed by the controller of the embodiment.

FIG. 6 is an explanatory view showing the structure of an oxygen enriching apparatus of another embodiment.

DESCRIPTION OF REFERENCE NUMERALS

1: oxygen enriching apparatus
19a, 19b, 19: adsorption tubes
17a, 17b, 17: directional control valves
33, 37: product tanks
31a, 31b, 35, 39: check valves
45, 61: electromagnetic valves
47, 63: flow-rate setting units
55, 65: pressure sensors
59, 67: controllers

DETAILED DESCRIPTION OF THE PREFERRED EMBODIMENTS

An example mode (embodiment) of the oxygen enriching apparatus, controller, and recording medium of the present invention will be described with reference to the drawings. However, the present invention should not be construed as being limited thereto.
(Embodiment)

The embodiment will be described, taking an oxygen enriching apparatus for medical use (hereinafter referred to as an "oxygen enriching apparatus") which has a built-in controller as an example.

The oxygen enriching apparatus of the present embodiment enriches oxygen contained in air through adsorption removal of nitrogen from the air and continuously supplies an oxygen-enriched gas to a patient, which is a user, at a first flow rate (e.g., 2 liters/min), which is equal to or less than a continuous base flow rate. Further, in case of need, the oxygen enriching apparatus switches its operation to breath-synchronized operation in order to supply the oxygen-enriched gas only during each inhalation period at a second flow rate (e.g., 6 liters/min), which is greater than the continuous base flow rate.

a) First, the basic structure of the oxygen enriching apparatus will be described.

As shown in FIG. 1, the oxygen enriching apparatus 1 of the present embodiment is accommodated in a main-body case 3. In an air introduction passage 5 are provided, in the sequence given from the upstream end, an air intake port 7, an intake air filter 9 for removing dust and dirt, a sound absorber 11 for lowering sound generated upon intake of air, a compressor 13 for compressing air, a heat exchanger 15 for cooling compressed air, a pair of directional control valves 17a and 17b (collectively denoted by 17) for switching between three flow passages, and a pair of adsorption tubes 19a and 19b (collectively denoted by 19).

A sirocco fan 21 for cooling the compressor 13 and the heat exchanger 15 is provided in the vicinity thereof.

A sound absorber 25 similar to the above and a silencer 27 for eliminating intermittent exhaust noise are provided in a discharge passage 23, which extends from the directional control valves 17 and is adapted to discharge nitrogen from the pair of adsorption tubes 19.

Moreover, in a supply passage 29, which extends from the pair of adsorption tubes 19 and is adapted to supply oxygen-enriched gas, are provided, in the sequence given from the upstream side, a pair of check valves 31a and 31b for preventing reverse flow toward the adsorption tubes 19, a first product tank 33 for storing oxygen-enriched gas, a check valve 35 for preventing reverse flow toward the first product tank 33, a second product tank 37 for storing oxygen-enriched gas, a check valve 39 for preventing reverse flow toward the second product tank 37, a regulator 41 for lowering the pressure of oxygen, a bacteria filter 43 for preventing passage of bacteria or the like, an electromagnetic valve 45 for opening/closing a flow passage, a flow-rate setting unit 47 for setting a supply flow rate of oxygen-enriched gas, and an oxygen outlet 49 for supplying oxygen-enriched gas.

An oxygen sensor 51 for detecting oxygen concentration is disposed between the check valve 39 and the regulator 41; and a pressure sensor 55 for detecting pressure at the time of inhalation is disposed between the flow-rate setting unit 47 and the oxygen outlet 49.

As shown by a broken line in FIG. 1, in the oxygen enriching apparatus 1 of the present embodiment, not only the compressor 13 but also the intake air filter 9, the sound absorbers 11 and 25, the heat exchanger 15, the directional control valves 17, the silencer 27, and the sirocco fan 21 are accommodated within a metal case 57 lined with vibration-absorbing rubber and a sound-absorbing material to thereby reduce noise during operation.

The oxygen enriching apparatus 1 having the above-described structure is a small apparatus whose continuous base flow rate is 2 liters/min. The apparatus has a weight of 30 kg, a power consumption of 170 W, and operating noise of 30 dB or less.

b) Next, the above-described respective components will be described in more detail.

Each of the above-described directional control valves 17 is a three-port directional control valve which operates under control of a controller 59. Through changeover operation, the directional control valves 17 selectively create a state in which the communication between the heat exchanger 15 and the adsorption tubes 19 is established and the communication between the adsorption tubes 19 and the discharge passage 23 is broken, and a state in which the communication between the heat exchanger 15 and the adsorption tubes 19 is broken and the communication between the adsorption tubes 19 and the discharge passage 23 is established.

The pair of adsorption tubes 19 are filled with a zeolite-containing adsorbent. This adsorbent has characteristics such that when pressurized (to, e.g., 2 atm (gauge pressure)), the adsorbent preferentially adsorbs nitrogen contained in air; and when the pressure is lowered (to, e.g., atmospheric pressure), the adsorbent releases the adsorbed nitrogen in order to self-regenerate.

The product tanks 33 and 37 each have a capacity of 750 ml and form a reservoir for oxygen-enriched gas.

That is, the product tanks 33 and 37 suppress variations in supply amount of oxygen-enriched gas to thereby enable continuous supply. Further, even when oxygen-enriched gas is supplied intermittently at a high flow rate, the product tanks 33 and 37 secure a sufficient supply capacity and prevent pressure fluctuations due to start and stop of supply of oxygen-enriched gas from propagating to the adsorption tubes 19.

The reason why the capacities of the product tanks 33 and 37 are set to 750 ml is that at 2 atm the two product tanks 33 and 37 can store 1.5 liters of oxygen-enriched gas in total, which is equivalent to 4.5 liters (maximum) at atmospheric pressure, and this tank capacity enables supply of oxygen-enriched gas at a rate of 6.5 liters/min during each inhalation period, which is the sum of a continuous base flow rate (2 liters/min) and the maximum supply capacity of the product tanks 33 and 37 (4.5 liters/min), if the time for storing the oxygen-enriched gas is sufficiently long. Notably, when the ratio between the inhalation period and the exhalation period is 1:2, oxygen-enriched gas can be supplied at a flow rate of 6 liters/min (maximum).

The check valve 35 disposed between the product tanks 33 and 37, in cooperation with the function of the product tanks 33 and 37, prevents propagation of pressure fluctuations to the adsorption tubes 19, which propagation would otherwise occur when oxygen-enriched gas is intermittently supplied at a high flow rate.

The regulator 41 reduces the pressure of oxygen-enriched gas from 2 atm, at which oxygen-enriched gas is supplied from the production tanks 33 and 37, to 0.35 atm (gauge pressure), at which a patient inhales the gas with ease.

The flow-rate setting unit 47 enables manual flow-rate setting.

That is, by adjusting an orifice, the continuous flow rate (first flow rate) can be set within a range up to the continuous base flow rate (2 liters/min). When a flow rate greater than the continuous base flow rate is set, oxygen-enriched gas cannot be supplied continuously. Therefore, the control is switched to breath-synchronized control in order to enable supply of oxygen-enriched gas at the set flow rate (second flow rate). Specifically, the breath-synchronized control is performed and the orifice is adjusted in accordance with the set flow rate to thereby enable supply of oxygen-enriched gas at the set flow rate.

A tube extending from an unillustrated cannula (nasal cannula) used by a patient is connected to the oxygen outlet 49. Accordingly, oxygen-enriched gas is supplied from the oxygen outlet 49 at a predetermined flow rate (first or second flow rate) set by use of the flow-rate setting unit 47 and under pressure reduced to 0.35 atm by means of the regulator 41.

c) Next, the electrical configuration of the controller 59 and other components for controlling the oxygen enriching apparatus 1 will be described.

In the present embodiment, as shown in FIG. 2, the controller 59 includes a microcomputer as a main element and is disposed inside the oxygen enriching apparatus 1. The controller 59 includes a CPU 59a, ROM 59b, RAM 59c, an input/output section 59d, a bus line 59e, etc., which are well known.

The flow-rate setting unit 47, the oxygen sensor 51, and the pressure sensor 53 are connected to the input/output section 59d of the controller 59. Further, the directional control valves 17 and the electromagnetic valve 45 are connected to the input/output section 59d as actuators.

Thus, the controller 59 performs a predetermined calculation on the basis of signals obtained from the flow-rate setting unit 47, the oxygen sensor 51, and the pressure sensor 53, and controls the operations of the directional control valves 17 and the electromagnetic valve 45.

d) Next, major functions of the oxygen enriching apparatus 1 according to the present embodiment will be described.

(1) Oxygen Enriching Function

In the present embodiment, by means of the directional control valves 17, the connections among the heat exchanger 15, the adsorption tubes 19, and the discharge passage 23 are switched in order to change the pressure applied to the adsorption tubes 19 to thereby enrich oxygen contained in air.

For example, a state in which one adsorption tube 19a communicates with the heat exchanger 15 via one directional control valve 17a is established, and compressed air is fed to the adsorption tube 19a by the compressor 13 to thereby apply pressure to the adsorption tube 19a. At this time, the communication between the adsorption tube 19a and the discharge passage 23 is broken by means of the directional control valve 17a.

Upon application of pressure, inside the adsorption tube 19a, nitrogen contained in air is adsorbed by the adsorbent, so that oxygen is enriched, and oxygen-enriched gas is supplied to the supply passage 29.

When the pressure of the adsorption tube 19a reaches about 2 $kg/cm^2$ (about 2 atm), which is the highest pressure for nitrogen adsorption, the other directional control valve 17b is operated in order to increase the internal pressure of the adsorption tube 19b in a similar manner. At this time, the communication between the adsorption tube 19a and the discharge passage 23 is established by means of the directional control valve 17a.

Through the above-described changeover, the internal pressure of the adsorption tube 19a communicating with the discharge passage 23 decreases to atmospheric pressure. Therefore, nitrogen is released from the adsorbent, and the adsorbent is regenerated. At the same time, the released nitrogen is discharged to the outside via the discharge passage 23 as the internal pressure of the adsorption tube 19 decreases.

When pressure is repeatedly applied to the two adsorption tubes 19 alternately through control of the two directional control valves 17 in the above-described manner, enriched oxygen of 90% or greater (about 90 to 95%) can be supplied continuously.

That is, these adsorption tubes 19 make it possible to extract oxygen solely upon application of pressure, and to supply oxygen of high concentration to the oxygen outlet 49 via the first and second product tanks 33 and 37 located downstream of the adsorption tubes 19.

The directional control valves 17 are switched at a timing at which the internal pressure of the adsorption tubes 19 reaches 2 atm. In the present embodiment, instead of using a pressure sensor for determining the timing, a timer is used in order to perform the switching.

That is, since the performance of the compressor 13 does not change very much, the internal pressure of the adsorption tubes 19 reaches 2 atm after passage of a predetermined period of time. Accordingly, every time the predetermined period of time has elapsed, the directional control valves 17 are switched to thereby change the adsorption tube 19 to be pressurized and the adsorption tube 19 from which nitrogen is to be discharged.

(2) Breath Synchronization Function

The highly-sensitive pressure sensor (e.g., a semiconductor pressure sensor) 55 connected to the vicinity of the oxygen outlet 49 detects a slight negative pressure (0.4 mmH$_2$O) which is produced when the patient inhales oxygen via the cannula. In response to detection of the negative pressure, the controller 59 opens and closes the electromagnetic valve 45 such that oxygen-enriched gas is supplied over the inhalation period of each breathing cycle of the patient, as shown in FIG. 3.

In the case of a human, in general, each inhalation period accounts for ⅓ of a corresponding breathing cycle, and each exhalation period accounts for ⅔ of the corresponding breathing cycle. Therefore, oxygen-enriched gas is supplied during the inhalation period only at the high flow rate, which is higher than the continuous base flow rate.

Through the above-described operation, oxygen-enriched gas is supplied to the patient only when the patient inhales oxygen, and the supply of oxygen-enriched gas is stopped during each exhalation period. Thus, during each exhalation period, oxygen-enriched gas can be stored in the product tanks 33 and 37.

In other words, since the capacity of the oxygen enriching apparatus 1 is 2 liters/min (2 liter model), when the patient needs a flow rate greater than 2 liters/min, electrical changeover is effected in order to provide breath-synchronized operation. Thus, in an example case in which inhalation is ⅓ and exhalation is ⅔, it becomes possible to supply oxygen-enriched gas at a high flow rate of 6 liters/min (total flow rate) through utilization of oxygen-enriched gas (4 liters) stored in the product tanks 33 and 37.

As shown in FIG. 3, since inhalation is not performed immediately before the end of each inhalation period (one third of each breathing cycle in the case of human), no great effect is achieved even when the oxygen-enriched gas is supplied at the set flow rate. However, the length of the period for supplying oxygen-enriched gas is set to about one third of that of the breathing cycle in order to make the manner of supply resemble to that of a continuously supply type to the extent possible, to thereby prevent the patient from feeling unnatural sensation.

Moreover, in the present embodiment, the controller 59 detects inhalation by use of the pressure sensor 55; calculates an averaged breathing cycle time from an average value of the past two to five breathing cycle times; regards one-third of the averaged breathing cycle time as an inhalation period; and opens the electromagnetic valve 45 over the inhalation period to thereby supply oxygen-enriched gas to the patient.

e) Next, a main portion of control processing performed in the controller 59 of the present embodiment will be described with reference to the flowchart shown in FIG. 4.

(1) Basic Control for Flow-rate Setting

First, the basic control for setting a supply flow rate by use of the flow-rate setting unit 47 will be described.

In step 100 of FIG. 4, the controller 59 makes a judgment as to whether the flow rate set by use of the flow-rate setting unit 47 is equal to or less than the continuous base flow rate (2 liter/min). When the result of judgment is "Yes", the controller 59 proceeds to step 110. When the result of judgment is "No", the controller 59 proceeds to step 120.

In step 110, the controller 59 controls the orifice in accordance with the set flow rate (first flow rate) and supplies oxygen-enriched gas continuously, because the set flow rate is a low flow rate of not greater than 2 liter/min, and therefore, the controller 59 judges that the breath-synchronized operation is not required; i.e., continuous supply must be effected. Subsequently, the controller 59 suspends the present processing. Notably, the electromagnetic valve 45 is in an opened state during this operation.

In step 120, the same processing as that in step 110 is performed up to the point where the controller 59 adjusts the orifice in accordance with a high flow rate (second flow rate) greater than 2 liters/min. In this case, the controller 59 judges that breath-synchronized operation is to be performed, i.e., oxygen-enriched gas must be supplied during the inhalation period only of each breathing cycle. Therefore, oxygen-enriched gas is accumulated in the product tanks 33 and 37 until the electromagnetic valve 45 is opened, by means of breath-synchronized operation, which will be described later. Notably, at that time, the electromagnetic valve 45 is in a closed state.

In subsequent step 130, in order to detect the timing of inhalation of the patient, the controller 59 performs processing for obtaining the pressure in the vicinity of the oxygen outlet 49 of the supply passage, on the basis of the signal from the pressure sensor 55.

In subsequent step 140, the controller 59 controls (i.e., opens and closes) the electromagnetic valve 45 in order to perform breath-synchronized operation. That is, as will be described below, the controller 59 performs the control in order to supply oxygen-enriched gas during the inhalation period only of each breathing cycle and stops the supply of oxygen-enriched gas during the exhalation period. Subsequently, the controller 59 suspends the present processing.

(2) Control of the Electromagnetic Valve 45

Next, control of the electromagnetic valve 45 performed in the above-described step 140 will be described.

In step 200 of FIG. 5, on the basis of the result of detection performed by the pressure sensor 55, the controller 59 judges whether inhalation has started. When the result of judgment is "Yes," the controller 59 proceeds to step 210. When the result of judgment is "No," the controller 59 suspends the present processing. That is, when the pressure decreases to a predetermined reference value (e.g., −0.4 mmH$_2$O) or less, the controller 59 judges that inhalation has started.

In step 210, the controller 59 opens the electromagnetic valve 45, because the patient has started inhalation.

In subsequent step 220, the controller 59 stores in, for example, RAM 59c the timing (time) at which start of the inhalation was detected.

In subsequent step 230, the controller 59 judges whether the number of breathing cycles having been performed after the control was switched to the breath-synchronized control is equal to or less than a predetermined number (e.g., 3). When the result of judgment is "Yes," the controller 59 proceeds to step 240. When the result of judgment is "No," the controller 59 proceeds to step 270.

In step 240, since the breathing cycle has been performed twice or less, the controller 59 uses a fixed value representing a preset timing (e.g., 4 seconds from the start of inhalation) as a timing for closing the electromagnetic valve 45 (i.e., a timing of end of a corresponding inhalation period).

The reason why 4 seconds is used as the fixed value is as follows. Although in the case of a human the number of times of breathing (per min) is typically 20 times on average, the number of times of breathing is expected to vary within a range of 5 to 50 times. In the slowest case (5 times), the length of each breathing cycle is 12 sec, and the length of each inhalation period is one-third thereof; i.e., 4 seconds. The length of this longest inhalation period is used as the fixed value.

In subsequent step 250, the controller 59 waits until the inhalation period ends.

In step 260, since the inhalation period has ended, the controller 59 closes the electromagnetic valve 45 to thereby stop supply of oxygen-enriched gas. Subsequently, the controller 59 suspends the present processing.

Meanwhile, when the controller 59 proceeds to step 270 as a result of the negative judgment in the above-mentioned step 230, this means that start of inhalation has been detected three times or more (i.e., two breathing cycles have been detected). Therefore, the controller 59 obtains an average length of the breathing cycles from data regarding the timing of inhalation in the two breathing cycles, and divides the average length by three to thereby obtain the length of each inhalation period. The average length is regularly updated to the latest value through calculation which is performed after addition of data of the latest breathing cycle.

In subsequent step 280, the controller 59 sets the inhalation-period length calculated in step 270 as a timing for closing the electromagnetic valve 45 (i.e., the timing of end of the corresponding inhalation period). Thus, the length of time between the start and end of the corresponding inhalation period is set.

Subsequently, similar to the above-described case, the controller 59 proceeds to step 250 and waits until the inhalation period ends; and in subsequent step 260 closes the electromagnetic valve 45 at the timing of end of the inhalation period to thereby stop supply of oxygen-enriched gas. Subsequently, the controller 59 suspends the present processing.

f) As described above, the oxygen enriching apparatus 1 according to the present embodiment is a small apparatus capable of continuously supplying oxygen-enriched gas at 2 liters/min. However, when a flow rate greater than the continuous base flow rate is set by use of the flow-rate adjusting unit 47, the oxygen enriching apparatus 1 automatically starts breath-synchronized control in order to supply oxygen-enriched gas to the patient at a high flow rate of 6 liters/min over each inhalation period.

That is, during each inhalation period, not only oxygen-enriched gas of the continuous base flow rate but also oxygen-enriched gas which was accumulated in the product tanks 33 and 37 in a previous exhalation period are supplied. Therefore, in spite of a small apparatus size, the oxygen enriching apparatus can supply the oxygen-enriched gas at a high flow rate over each inhalation period.

Accordingly, the oxygen enriching apparatus 1 of the present embodiment achieves the following advantageous effects. (1) Since the volume and weight of the oxygen enriching apparatus do not increase, the burden imposed on a sales representative or a caregiver can be decreased. (2) Since electrical-power consumption does not increase, electricity cost is low. (3) Since the level of noise is low, the noise does not hinder good sleep of the patient. In addition, even when a measure against noise is employed, the volume and weight of the oxygen enriching apparatus do not increase very much.

In addition, in the present embodiment, data regarding breathing cycles of the patient are accumulated, and the length of each inhalation period is obtained from the data. Therefore, an accurate value for the length of each inhalation period can be obtained.

Moreover, since oxygen-enriched gas is supplied at a high flow rate over the entirety of the inhalation period which has a length equal to ⅓ of that of each breathing cycle and is obtained from data, the patient feels reduced unnatural sensation, as compared with the case in which oxygen is supplied in a pulse form (in the case of an oxygen cylinder being used).

Moreover, in the present embodiment, the product tanks (750 ml) 33 and 37 are disposed in series, and the check valve 35 is disposed between them. Therefore, even when oxygen-enriched gas is supplied intermittently by means of the breath-synchronized control and thus a pressure fluctuation occurs, the pressure fluctuation can be prevented from propagating to the adsorption tubes 19.

The present invention is not limited to the above-described embodiment, and may be practiced in various forms without departing from the scope of the present invention.

(1) In the above-described embodiment, an oxygen enriching apparatus and a controller therefore have been described. However, the present invention is not limited thereto, and encompasses a recording medium which stores means for executing the above-described processing.

Examples of such a recording medium include a microchip, a floppy disk, a hard disk drive, an optical disk, and electronic control devices (ROM, RAM, EPROM, EEPROM, etc.) which are incorporated in a microcomputer. In other words, no limitation is imposed on the recording medium, insofar as the selected recording medium stores means, such as a program, which can execute the above-described processing of the oxygen enriching apparatus and the controller.

(2) The above-described embodiment exemplifies the case in which the controller is built in the oxygen enriching apparatus. However, the controller may be separate from the oxygen enriching apparatus.

For example, as shown in FIG. 6, a controller unit 69 including an electromagnetic valve 61, a flow-rate setting unit 63, a pressure sensor 65, a controller 67, etc. may be separated from a main body case 3, which accommodates the remaining large components such as the compressor 13 and the adsorption tubes 19.

In such a case, a tube 73 serving as a passage for supplying oxygen-enriched gas is extended from the oxygen outlet 49 of the main body case 3 to an oxygen inlet 71 of the controller unit 69; and a tube extending from an unillustrated cannula is connected to an oxygen outlet 75 provided on the controller unit 69.

Since the controller 69 can be disposed near a patient or any other person, operation is facilitated.

Notably, the components which are separated from the main body case 3 and incorporated in the controller unit 69 can be selected freely in consideration of the size of the controller unit 69 and other factors.

(3) Moreover, in the above-described embodiment, a period in which oxygen-enriched gas is supplied during breath-synchronized operation is determined to completely match the inhalation period. However, that period may be set to be slightly shorter or longer than the inhalation period, insofar as oxygen-enriched gas can be supplied in a sufficient amount at which a user does not feel any unnatural sensation.

EFFECTS OF THE INVENTION

Most (about 85%) of patients suffering chronic respiratory disease are satisfied with use of an oxygen enriching apparatus (2 liter model) whose flow rate is 2 liters/min or less. However, when their condition becomes worse, they require an oxygen enriching apparatus (5 liter model) whose flow rate is 5 liter/min or more. Having two types of oxygen enriching apparatuses is not economical.

By contrast, the present invention enables a small apparatus (e.g., a 2 liter model) to supply oxygen-enriched gas at a high flow rate of, for example, 5 liters/min or greater. Therefore, having one oxygen enriching apparatus is sufficient, which is very economical.

A 5 liter model imposes a greater burden on a patient, a caregiver, and a sales representative as compared with a small apparatus, because of its heavy weight, large electrical power consumption, and large operation noise, and is uneconomical. By contrast, since the oxygen enriching apparatus of the present invention is small in size, such problems will not arise.

Moreover, in the present invention, when breath-synchronized operation is performed, oxygen-enriched gas is supplied over each inhalation period to thereby make the manner of supply resemble to that of a continuously supply type to a possible extent. Therefore, a user hardly feels unnatural sensation.

In other words, the oxygen enriching apparatus of the present invention has the advantages of a small oxygen enriching apparatus (e.g., 2 liter model), and serves as an all-purpose oxygen enriching apparatus which can also be used as a large oxygen enriching apparatus (e.g., 5 liter model).

This application is based on Japanese Patent Application No. 2000-287108 filed Sep. 21, 2000, the disclosure of which is incorporated herein by reference in its entirety.

What is claimed is:

1. An oxygen enriching apparatus which enriches oxygen contained in the air to thereby obtain oxygen-enriched gas, and which supplies the oxygen-enriched gas to a user synchronously with inhalation of the user by means of a breath synchronizing function, which comprises:

means for supplying the oxygen-enriched gas at a first flow rate of up to 4 liters/min equal to or less than a continuous base flow rate when a breath-synchronized operation is not performed, wherein the continuous base flow rate is a flow rate at which the oxygen enriching apparatus can supply the oxygen-enriched gas continuously; and means for supplying the oxygen-enriched gas at a second flow rate of 5 to 7 liters/min greater than the continuous base flow rate over an inhalation period having a length 25 to 40% that of a breathing cycle of the user when a breath-synchronized operation is performed.

2. The oxygen enriching apparatus as claimed in claim 1, which comprises means for detecting the state of inhalation or exhalation including a sensor, and for controlling supply of the oxygen-enriched gas based on a signal output from the sensor.

3. The oxygen enriching apparatus as claimed in claim 2, which comprises means for determining a timing for starting or ending supply of the oxygen-enriched gas in the breathing cycle, based on the sensor signal.

4. The oxygen enriching apparatus as claimed in claim 3, which comprises means for detecting the state of inhalation or exhalation one time or a plurality of number of times on the basis of a signal output from the sensor, and for determining the timing for starting or ending subsequent supply of the oxygen-enriched gas based on the thus-detected state of inhalation or exhalation.

5. The oxygen enriching apparatus as claimed in claim 1, comprising a tank provided in an oxygen-enriched-gas supply passage on the downstream side of an oxygen enriching section, for accumulating oxygen-enriched gas supplied during the exhalation period of each breathing timing.

6. The oxygen enriching apparatus as claimed in claim 1, comprising a plurality of tanks provided in series in an oxygen-enriched-gas supply passage, on the downstream side of an oxygen enriching section, for stably supplying the oxygen-enriched gas.

7. The oxygen enriching apparatus as claimed in claim 6, wherein each of two tanks connected in series has a capacity of at least 500 ml.

8. The oxygen enriching apparatus as claimed in claim 6, comprising a check valve for preventing reverse flow toward the oxygen enriching section disposed between the plurality of tanks.

9. The oxygen enriching apparatus as claimed in claim 1, comprising a switch for setting a flow rate of the oxygen-enriched gas, wherein when the flow rate is set by use of the switch to the first flow rate equal to or less than the continuous base flow rate, the oxygen enriching apparatus supplies the oxygen-enriched gas continuously, and when the flow rate is set by use of the switch to the second flow rate greater than the continuous base flow rate, the oxygen enriching apparatus supplies the oxygen-enriched gas by means of the breath-synchronized operation.

10. A controller for controlling operation of an oxygen enriching apparatus which enriches oxygen contained in the air to thereby obtain oxygen-enriched gas, and which supplies the oxygen-enriched gas to a user synchronously with inhalation of the user by means of a breath synchronizing function, which oxygen-enriching apparatus comprises:

means for supplying the oxygen-enriched gas at a first flow rate of up to 4 liters/min equal to or less than a continuous base flow rate when a breath-synchronized operation is not performed, wherein the continuous base flow rate is a flow rate at which the oxygen enriching apparatus can supply the oxygen-enriched gas continuously; and means for supplying the oxygen-enriched gas at a second flow rate of 5 to 7 liters/min greater than the continuous base flow rate over an inhalation period having a length 25 to 40% that of a breathing cycle of the user when a breath-synchronized operation is performed.

11. A recording medium having recorded thereon means for executing the function of a controller for controlling operation of an oxygen-enriching apparatus which enriches oxygen contained in the air to thereby obtain oxygen-enriched gas, and which supplies the oxygen-enriched gas to a user synchronously with inhalation of the user by means of a breath synchronizing function, which oxygen-enriching apparatus comprises:

means for supplying the oxygen-enriched gas at a first flow rate of up to 4 liters/min equal to or less than a continuous base flow rate when a breath-synchronized operation is not performed, wherein the continuous base flow rate is a flow rate at which the oxygen enriching apparatus can supply the oxygen-enriched gas continuously; and means for supplying the oxygen-enriched gas at a second flow rate of 5 to 7 liters/min greater than the continuous base flow rate over an inhalation period having a length 25 to 40% that of a breathing cycle of the user when a breath-synchronized operation is performed.

* * * * *